US008119119B2

(12) United States Patent
Mallet et al.

(10) Patent No.: US 8,119,119 B2
(45) Date of Patent: Feb. 21, 2012

(54) NON-INTEGRATIVE AND NON-REPLICATIVE LENTIVIRUS, PREPARATION AND USES THEREOF

(75) Inventors: Jacques Mallet, Paris (FR); Che Serguera, Rome (IT); Stéphanie Philippe, Paris (FR); Chamsy Sarkis, Boulogne Billancourt (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 924 days.

(21) Appl. No.: 11/628,534

(22) PCT Filed: Jun. 24, 2005

(86) PCT No.: PCT/FR2005/001604
§ 371 (c)(1),
(2), (4) Date: Feb. 5, 2007

(87) PCT Pub. No.: WO2006/010834
PCT Pub. Date: Feb. 2, 2006

(65) Prior Publication Data
US 2008/0089863 A1    Apr. 17, 2008

(30) Foreign Application Priority Data

Jun. 25, 2004  (FR) ...................................... 04 07017

(51) Int. Cl.
*C12N 15/867* (2006.01)
*C12N 15/00* (2006.01)
*C12N 15/48* (2006.01)
*A61K 48/00* (2006.01)

(52) U.S. Cl. ................... 424/93.2; 435/91.1; 435/91.33; 435/91.41; 435/91.42; 530/300; 424/199.1

(58) Field of Classification Search ........................ None
See application file for complete search history.

(56) References Cited

U.S. PATENT DOCUMENTS

2007/0042494 A1* 2/2007 Kafri et al. .................... 435/456
2009/0047339 A1* 2/2009 Barnett et al. ................ 424/450

FOREIGN PATENT DOCUMENTS

WO    97/31119    8/1997
WO    00/72886 A1    12/2000

OTHER PUBLICATIONS

Leavitt et al, Human Immunodeficiency Virus Type 1 Integrase Mutants Retain in Vitro Integrase Activity yet Fail to Integrate Viral DNA Efficiently during Infection, Journal of Virology, Feb. 1996, p. 721-728 vol. 70, No. 2.*
Spotlight on HIV-1 Integrase, PRN Notebook, 2006, vol. 11(3), pp. 10, downloaded Sep. 7, 2010.*
Cannon et al, Conserved Sequences in the Carboxyl Terminus of Integrase That Are Essential for Human Immunodeficiency Virus Type 1 Replication, Journal of Virology, Jan. 1996, p. 651-657.*
Leavitt et al., "Human immunodeficiency virus type 1 integrase mutants retain in vitro integrase activity yet fail to integrate viral DNA efficiently during infection", Journal of Virology, The American Society for Microbiology, vol. 70, No. 2, Feb. 1996, pp. 721-728, XP002207365.
Wiskerchen et al., "Human immunodeficiency virus type 1 integrase: Effects of mutations on viral ability to integrate, direct viral gene expression from integrated viral DNA templates, and sustain viral propagation in primary cells", Journal of Virology, The American Society for Microbiology, vol. 69, No. 1, Jan. 1995, pp. 376-386, XP000560257.
Follenzi et al., "Gene transfer by lentiviral vectors is limited by nuclear translocation and rescued by HIV-1 pol sequences", Nature Genetics, Nature America, vol. 25, No. 2, Jun. 2000, pp. 217-222, XP002980776.

* cited by examiner

*Primary Examiner* — Maria Marvich
(74) *Attorney, Agent, or Firm* — Nixon & Vanderhye P.C.

(57) ABSTRACT

The invention concerns a non-integrative and non-replicative recombinant lentivirus as well as its uses, in particular for preparing a composition for transferring genes in vitro, ex vivo or in vivo. The invention is useful for transferring genes in any mammal organism, for example in liver, muscle, pancreas or central nervous system (including the ocular sphere) tissues or cells, and in particular for treating disorders or pathologies such as, for example, central nervous system, including the ocular sphere, disorders.

Figure 1:
Figure 1:
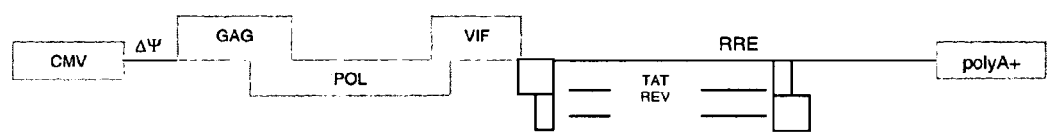
Figure 1:

12 Claims, 8 Drawing Sheets vector plasmid (pTrip CMV GFP)

Transcomplementation plasmid (p8.9)

envelope plasmid (pVSV-G)

NON-INTEGRATIVE AND NON-REPLICATIVE LENTIVIRUS, PREPARATION AND USES THEREOF

This application is the US national phase of international application PCT/FR2005/001604, filed 24 Jun. 2005, which designated the U.S. and claims priority of FR 0407017, filed 25 Jun. 2004, the entire contents of each of which are hereby incorporated by reference.

The present invention describes a non-integrative and non-replicative recombinant lentivirus as well as its uses, in particular for preparing a composition for transferring genes in vitro, ex vivo or in vivo. The invention is useful for transferring genes in any mammal organism, for example in liver, muscle, pancreas or central nervous system (including the ocular sphere) tissues or cells, and in particular for treating disorders or pathologies such as, for example, central nervous system, including the ocular sphere, disorders.

There are multiple applications for the transfer of genes in the nervous system, in particular in experimental (e.g. research) and therapeutic fields. Thus, this transfer can make it possible to perform studies of marking, toxicity, quality, the construction of pathological models, the restoration of deficiencies, the expression of therapeutic products (e.g. proteins, RNAs etc.) etc.

Different approaches have been considered in the prior art for this transfer such as the use of viral vectors (retrovirus, AAV, adenovirus, etc.), the injection of plasmids, cell transplantation, the implantation of encapsulated cells, etc. Each of these approaches has advantages and disadvantages in terms of efficiency, safety, industrial use, selectivity, stability, etc. Thus, the use of viral vectors is advantageous in terms of transfer efficiency, linked to the natural infection properties of viruses.

In this context, numerous retroviral vectors derived from oncoretrovirus enable integration of a transgene into the genome of target cells, but these vectors are only capable of transducing division cells. This restriction limits their use to the transfer of genes ex vivo or to organs of which the cells are mitotically active.

In order to overcome this obstacle, the use of vectors derived from lentivirus has been considered. In relation to the other viral vectors currently developed, lentiviral vectors offer several practical advantages including ease of production and increased knowledge of their biology. These vectors are widely used for transferring genes within the context of experimental gene therapy protocols. They make it possible to efficiently transduce numerous cell types, in particular quiescent cells of the central nervous system. In fact, lentiviruses are complex retroviruses capable of integrating into the genome of cells which are not mitotically active. Examples of these lentiviruses are the HIV-1, HIV-2, SIV, FIV, BIV, VISNA, CAEV and EIAV viruses. However, one disadvantage linked to the use of retroviruses, and in particular lentiviruses, lies in particular in the fact that they have a potential risk of insertional mutagenesis because they integrate into the chromatin of the transduced cells and, in an apparently preferential way, into encoding sequences. Up till now, this disadvantage has restricted the exploitation of this type of vector for transferring genes in vivo.

With the aim of reducing the risk of insertional mutagenesis, which at the current time is the major obstacle for the use of these vectors clinically, the inventors have developed a non-integrative and non-replicative lentiviral vector. The non-integrative character of this new generation of lentiviral vectors is therefore a considerable advance in terms of biosafety, in particular for gene therapy. This vector can be used, for example, for the stable expression of a transgene or other nucleic acids in cells which do not divide or for the transient expression of a gene in division cells resistant to other methods of transfection or even of transduction by other vectors.

Non-integrative vectors are known in the prior art, the most common of them being the adenoviral vectors and the herpetic vectors. However, for these types of vectors, there is at the current time no production method which makes it possible to obtain batches free from all replicative contaminants. Of the integrative vectors, the AAV vectors, although they only integrate with a relatively low frequency (approximately 10%), are limited by the size of the transgene which can be cloned to it and by the mutations which they also cause at their insertion site.

The present invention therefore offers a solution to the problems of the prior art and provides new tools and vectors for transferring genes in the nervous system.

The invention is concerned particularly with the perfection of a non-replicative and non-integrative recombinant lentivirus.

In general, the lentiviruses of the invention comprise a mutated integrase and a particular recombinant genome. More preferably, the lentiviruses according to the invention comprise (i) a recombinant genome comprising, between the LTR 5' and 3' lentiviral sequences, a lentiviral encapsidation psi sequence, a RNA nuclear export element, a transgene, and possibly a promoter and/or a sequence favouring the nuclear import of RNA, as well as (ii) a mutated integrase preventing the integration of said genome into the genome of a host cell. In one particular embodiment of the invention, the recombinant genome comprises, for example, the sequence 5'LTR-psi-RRE-cPPT CTS-transgene-LTR3'.

Another object of the invention relates to any pharmaceutical composition (including vaccinal composition) comprising a lentivirus according to the invention and a pharmaceutically acceptable excipient.

The invention also relates to methods and compositions for the in vitro, ex vivo and in vivo transfer of target genes in populations of particular cells, and also to the treatment of disorders, for example disorders of the central nervous system, including the ocular system.

Another object of the invention relates to the use of a non-integrative and non-replicative lentivirus, as defined above, for preparing a composition for transferring genes in a mammal cell (preferably human), preferably in a cell from the central nervous system (including the ocular sphere) of a subject in vitro, ex vivo or in vivo.

The object of the invention is also any method for producing a non-replicative and non-integrative lentivirus, as defined above, comprising in particular the introduction of a vector plasmid including, in cells, a recombinant genome, such as defined above, in the presence of appropriate transcomplementation functions, and in particular of a lentiviral pol region encoding a modified integrase, as defined above. The method can be implemented by the transient transfection of different transcomplementation and envelope plasmids, or in the presence of an auxiliary virus, and/or in cell lines expressing one or more of the complementation proteins.

The invention also relates to a line of cells expressing, in a stable manner, a preferably lentiviral integrase comprising a mutation which induces a loss of integration function of said integrase. The mutation, in the sense of the invention, can correspond to point mutations and/or to microdeletions of some bases of the integrase. It preferably corresponds to one or more point mutations affecting a basic region, the C-terminal region (for example a basic region of the C-terminal region) and/or the catalytic site of the integrase, said mutated integrase lacking integrative function.

One particular object of the invention therefore relates to a method of preparing a non-replicative and non-integrative recombinant lentivirus comprising the transfection of a cell using a non-integrative and non-replicative lentiviral vectorial system comprising:
a) a transcomplementation plasmid, lacking any psi encapsidation signal and comprising a lentiviral gag sequence and a mutated lentiviral pol sequence encoding an integrase which is non-functional for the integration, said plasmid possibly being deleted from the accessory genes such as vif, nef, vpu and/or vpr,
b) an envelope plasmid including a promoter-env-PolyA sequence, and
c) a lentiviral vector plasmid including a recombinant genome between the lentiviral LTR 5' and 3' sequences, a lentiviral encapsidation psi sequence, a RNA nuclear export element, a transgene, and possibly a promoter and/or a sequence favouring the nuclear import of RNA, as well as a mutated integrase preventing the integration of said genome into the genome of a host cell, said vector lacking any encoding sequence of the lentivirus,
and recovery of lentiviruses produced.

KEYS TO THE FIGURES

FIG. 1:
System for producing lentiviral vectors by transfection of three plasmids: a vector plasmid carrying the GFP transgene under the control of the human cytomegalovirus (hCMV) promoter and the central flap sequence [central polypurine tract—central termination sequence (cPPT-CTS)] which intervenes in the nuclear import, the RRE (REV Responsive Element) sequence which interacts with a REV regulation element and the psi encapsidation sequence ($\psi$), the LTR 3' U3 region has been deleted from the promoter sequence ($\Delta$U3); a transcomplementation plasmid expressing the proteins necessary for the precocious phases of the replicative cycle of VIH-1 (GAG and POL), regulation elements (TAT, REV) under the control of the CMV promoter and deleted from the iv sequence; an envelope plasmid expressing the envelope glycoprotein of the vesicular stomatitis virus (VSV-G) under the control of the CMV promoter.

Figure 2:
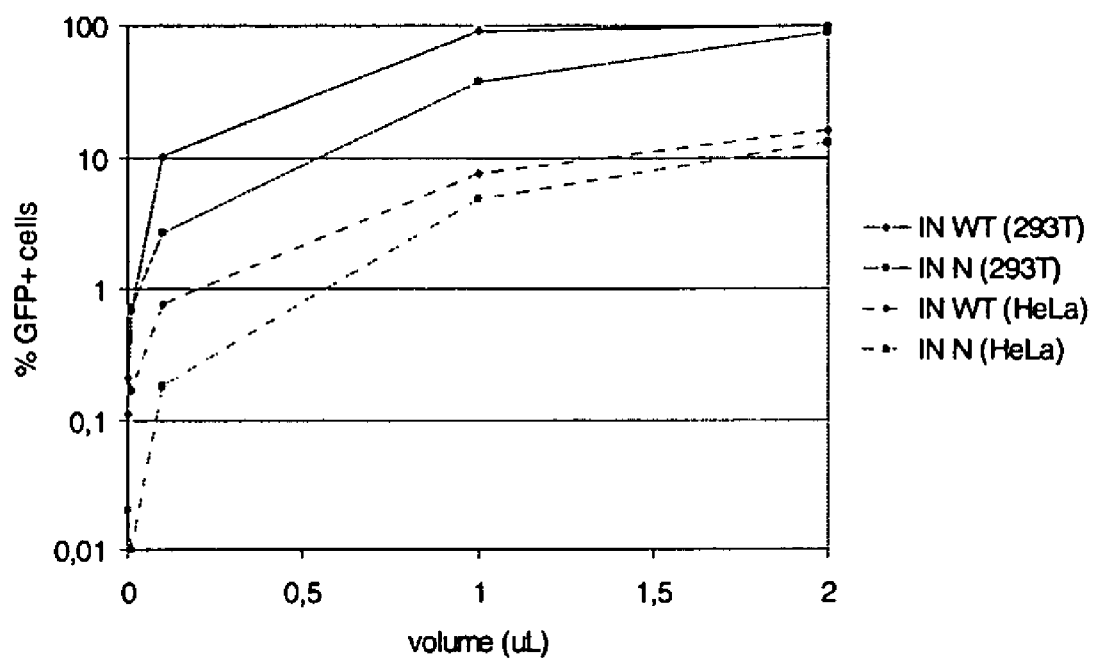

FIG. 2:
Expression of GFP obtained after transduction of cell lines (293T and HeLa) by a non-integrative lentiviral vector. The percentage transduction is determined by FACS 72 hrs after incubation of the cells in the presence of different doses (volume in microlitres per well) of an $IN_{WT}$ CMV GFP integrative and $IN_N$ CMV GFP non-integrative lentiviral vector.

Figure 3:
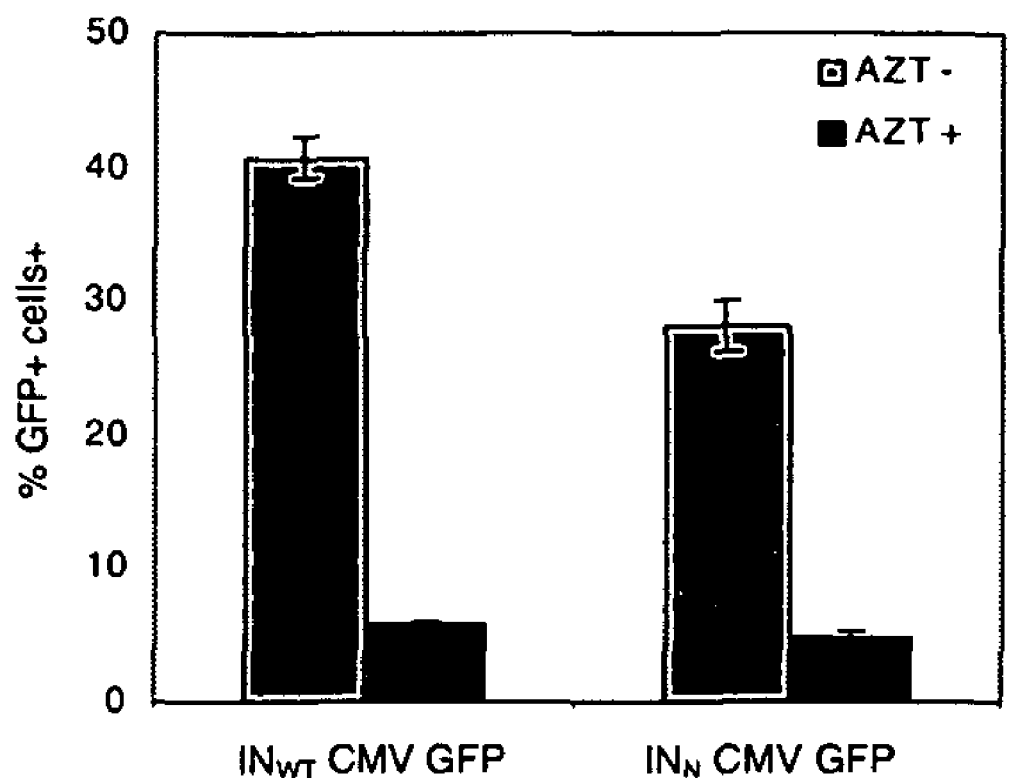

FIG. 3:
Inhibition of transduction by an $IN_{WT}$ CMV GFP integrative and $IN_N$ CMV GFP non-integrative lentiviral vector after treatment of the AZT cells. The percentage transduction was determined by FACS after 72 hrs incubation of the 293T cells in the presence of the vector on its own or of the vector and AZT 10 µM.

Figure 4:
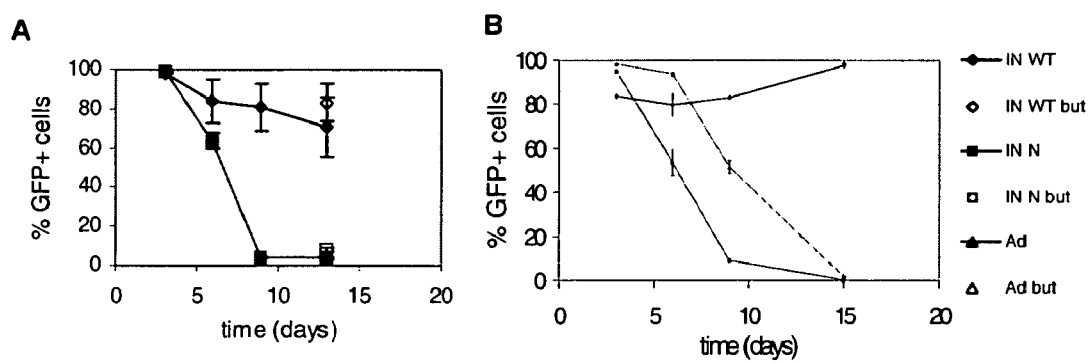

FIG. 4:
Expression of GFP during the time after transduction of cell lines (293T and MT4) with $IN_{WT}$ CMV GFP integrative and $IN_N$ CMV GFP non-integrative lentiviral vectors. The percentage of $GFP^+$ cells was determined by FACS (A: 293T, B: MT4) 3 days, 6 days, 9 days and 12 or 15 days after transduction (MOI 5). For the points noted "but": the cells have undergone 5 mM sodium butyrate treatment 24 hrs before analysis.

Figure 5:
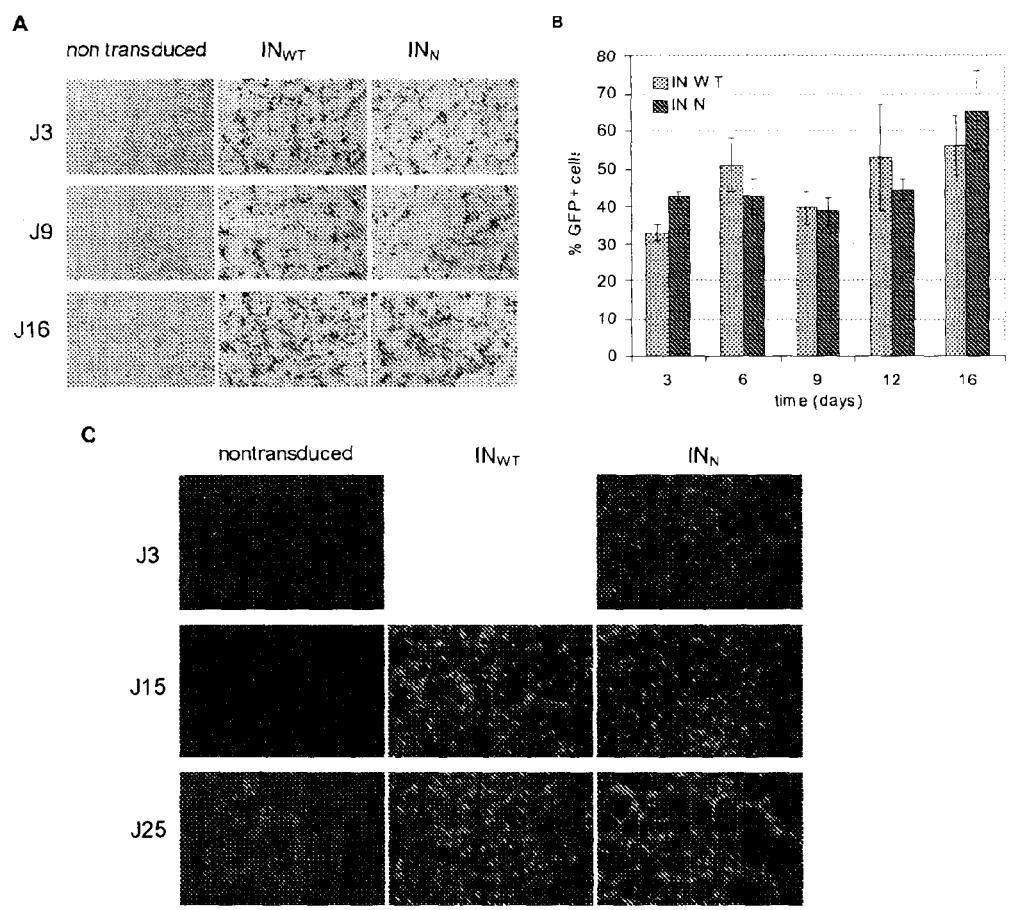

FIG. 5:
Expression of GFP in primary embryonic neurons taken from rat cortex after transduction by an $IN_{WT}$ CMV GFP integrative or IN CMV GFP non-integrative lentiviral vector
A: Immunocytochemical analysis of the expression in control (non-transduced) neurons, transduced by the integrative ($IN_{WT}$) vector or transduced by the non-integrative ($IN_N$) vector 3, 9 and 16 days after transduction (enlargement×20).
B: percentage transduction of the cortical neurons in $IN_{WT}$ and $IN_N$ groups. The measurements were taken in triplicate and expressed as averages±the standard error (SEM).
C: Immunocytofluorescent analysis of the expression in control (non-transduced) neurons, transduced by the integrative ($IN_{WT}$) vector or transduced by the non-integrative ($IN_N$) vector 3, 15 and 25 days after transduction (enlargement×10).

Figure 6:
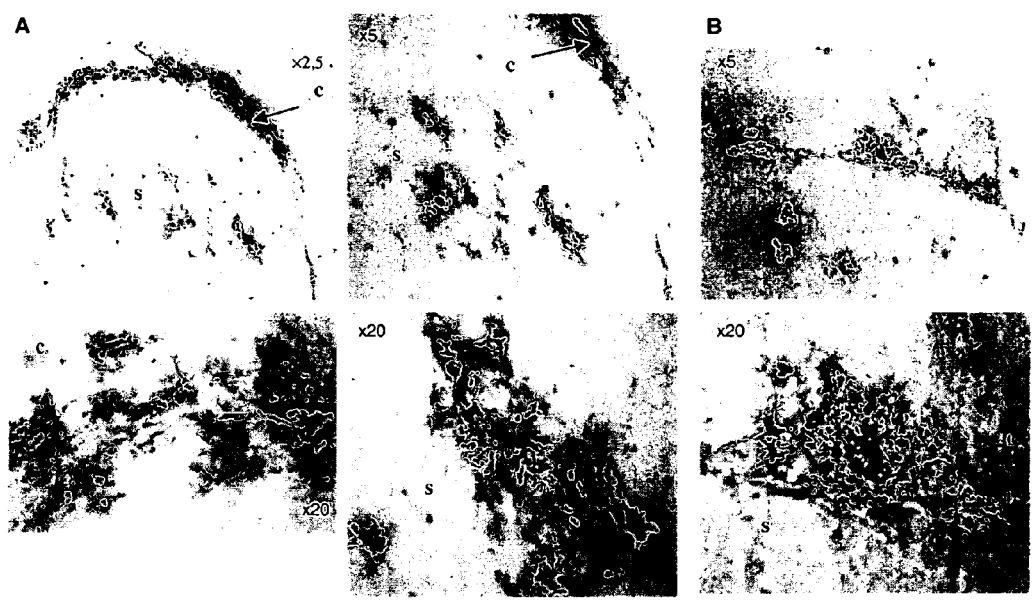

FIG. 6:
Expression of GFP in vivo after injection into the mouse striatum. The brain was removed 10 days after stereotaxic injection of the $IN_N$ CMV GFP (A) or $IN_{WT}$ CMV GFP (B) vector in the mouse striatum, cut with a cryostat with a 20 µm thick cut and analysed after immunohistochemistry so as to reveal the presence of GFP. cc: callous body, str: striatum. The enlargement (×2.5, ×5 or ×20) is indicated on each photograph.

Figure 7:
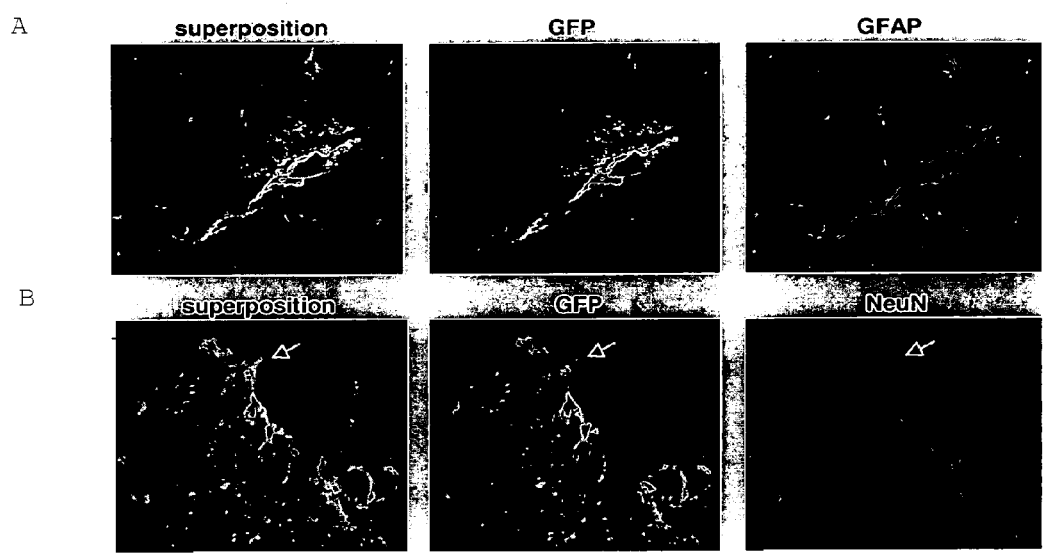
Figure 8:
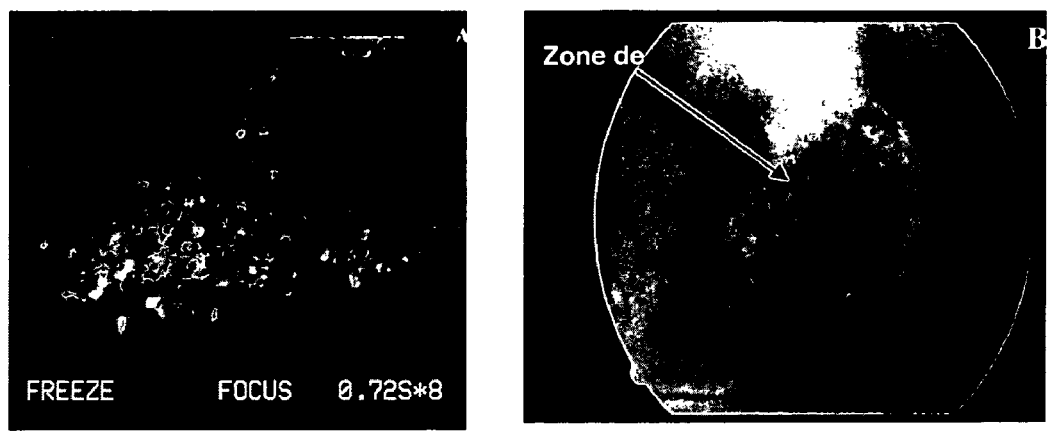

FIG. 7:
Expression of GFP in vivo after injection into the mouse striatum. The brain was removed 10 days after stereotaxic injection of the INN CMV GFP vector into the mouse striatum, cut with a cryostat with a 20 µm thick cut, and analysed after immunohistofluoresence with a confocal microscope.
A: CFP/GFAP co-marking: astrocyte expressing GFP (enlargement×40).
B: GFP/NeuN co-marking: neuron expressing GFP (enlargement×16). FIG. 8:
A: Expression of GFP in vivo in the rat after subretinal injection of 66 ng p24 of INN CMV GFP non-integrative lentiviral vector. Photograph with fluorescence microscopy (×2.5) on retina mounted flat 2 weeks after injection.
B: Expression of GFP in vivo in the dog after subretinal injection of 2.5 µg p24 of INN CMV GFP non-integrative lentiviral vector. Angiography in fluroescent light in vigil dog 1 month after injection.

DETAILED DESCRIPTION OF THE INVENTION

The present invention describes non-integrative and non-replicative recombinant lentiviruses enabling the transfer of genes in any mammal cell, in particular in human cells. These can be division cells or quiescent cells, cells belonging to central organs or to peripheral organs such as the liver, the pancreas, a muscle, the heart, etc. One particular object of the invention relates to the transfer of genes in the nervous system (including the ocular system) and in particular in neurons, astrocytary type glial cells and retinal cells, as well as in cancerous tumours. These lentiviral vectors are useful for the in vivo transfer and expression of nucleic acid sequences, in particular within the nervous system.

General Structure of the Vectors
Like other retroviruses, lentiviruses have gag, pol and env genes flanked by two LTR (Long Terminal Repeat) sequences. Each of these genes encodes for numerous proteins which are initially expressed in the form of a single precursor polypeptide. The gag gene encodes for the internal structure proteins (capsids and nucleocapsid). The pol gene encodes for inverse transcriptase, integrase and protease. The env gene encodes for viral envelope glycoprotein. Furthermore, the lentivirus genome contains a cis-acting RRE (Rev Responsive Element) element responsible for exporting out of the nucleus of the viral genomic RNA which will be packaged. The LTR 5' and 3' sequences serve to promote the transcription and polyadenylation of the viral RNAs. The LTR contains all of the other cis-acting sequences necessary for viral replication. Sequences necessary for the inverse transcription of the genome (linkage site of the RNAt primer) and for the encapsidation of viral RNA in particles (T site) are adjacent to the LTR 5'. If the sequences necessary for encapsidation (or for packaging retroviral RNA in the infectious virions) are absent from the viral genome, genomic RNA will not be actively packaged. Furthermore, the lentiviral genome comprises accessory genes such as vif, vpr, vpu, nef, TAT, REV etc.

The construction of lentiviral vectors for gene transfer applications has been described, for example, in patents U.S. Pat. No. 5,665,577, EP 386 882, U.S. Pat. No. 5,981,276, U.S. Pat. No. 6,013,516 or in patent applications WO99/58701 and WO02/097104. These vectors include a defective lentiviral genome, i.e. in which at least one of the gag, pol and env genes has been inactivated or deleted.

The lentiviral vector according to the invention is a non-replicative and non-integrative recombinant lentivirus, i.e. it is incapable of autonomous replication and specific integration in transduced cells. More particularly, the invention relates to a non-replicative and non-integrative recombinant lentivirus comprising a recombinant genome comprising, between the LTR 5' and 3' lentiviral sequences, a lentiviral encapsidation psi sequence, and a RNA nuclear export element, a transgene and possibly a promoter and/or a sequence favouring the nuclear import of RNA, as well as a mutated integrase preventing the integration of said genome into the genome of a host cell. The lentivirus according to the invention can include, for example, the sequence 5'LTR-psi-RRE-cPPT CTS-transgene-LTR3'.

One particular object of the invention relates to a lentivirus the genome of which is advantageously lacking any encoding lentiviral sequence.

One important feature of the lentiviruses of the invention is the fact that they comprise a modified integrase. This invention demonstrates, for the first time, that it is possible to produce, in effective conditions for the expression of a transgene, non-replicative recombinant lentiviruses, the integration properties of which are altered. The presence of a modified integrase results from the use, in order to produce the viruses of the invention, of a modified pol sequence such as to produce an integrase which is non-functional for the integration, but without any substantial effect upon the preceding steps of the vector cycle during the cellular transduction (so-called class 1 mutation). Therefore, the vector obtained has an episomal phenotype in so far as, advantageously, the mutation of the integrase does not prevent the progression of the genome towards the nucleus, nor its retrotranscription in the form of a linear DNA genome which can then circularise (formation of circles). In the sense of the invention, a class 1 mutation preferably consists of one or more point mutations, preferably affecting the nucleic acid portion encoding a basic region, the C-terminal region (preferably a basic region of the C-terminal region) and/or the catalytic site of the integrase. The point mutation preferably corresponds to the substitution of an amino acid by another in the encoded sequence of the integrase. The mutation is preferably non-conservative in the sense that it makes the integrase non-functional for the integration. Such a mutation is preferably chosen from the mutants producing an integrase which is non-functional for the integration, while conserving the other functions of the integrase, e.g. those involved in the progression of the vector towards the nucleus. Examples of mutations affecting HIV-1 and making it possible to obtain a non-functional integrase for the integration are the following:

H12N, H12C, H16C, H16V, S81R, D41A, K42A, H51A, Q53C, D55V, D64E, D64V, E69A, K71A, E85A, E87A, D116N, D1161, D116A, N120G, N1201, N120E, E152G, E152A, D-35-E, K156E, K156A, E157A, K159E, K159A, K160A, R166A, D167A, E170A, H171A, K173A, K186Q, K186T (L region of the C-terminal basic region), K188T, E198A, R199C, R199T, R199A, D202A, K211A, Q214L (214 and 216 belong to the Q region of the C-terminal basic region), Q216L, Q221L, W235F, W235E, K236S, K236A, K246A, G247W, D253A, R262A, R263A (N region of the C-terminal basic region) and K264H.

The mutations affecting the catalytic site preferably relate, as regards HIV-1, to amino acids 64, 116 and/or 152 of the integrase. The mutations affecting the C-terminal portion of this lentivirus are advantageously chosen from the substitution of the $_{262}$RRK motif by AAH, a substitution in the Q region (Q214L and/or Q216L), in the L region (K186) and/or in the L region. A preferred mutation consists of the substitution of the $_{262}$RRK motif by AAH.

The lentiviruses of the invention typically include a recombinant genome with the sequence 5'LTR-psi-RRE-cPPT CTS-(promoter)-transgene-LTR3'. The transgene is typically placed under the control of a promoter. One and/or the other can also be placed upstream of the cPPT CTS element.

The recombinant genome thus includes the cis-acting viral sequences, useful for encapsidation and for transduction. Advantageously, it only keeps certain lentiviral sequences, in particular

- those necessary for encapsidation of the genome (psi sequence of lentiviral origin);
- a RNA nuclear export element. The latter is advantageously chosen from the REV responsive element (RRE sequence for "REV Responsive Element") of a lentivirus genome, in particular of a VIH, and for example VIH-1 (the RRE sequence, present on viral RNA, interacts with a REV regulation element), CTE ("Constitutive Transport Element") of the Mason Pfizer Monkey virus, a SIV, HIV-2 or FIV nuclear export system, or an element equivalent to any other retrovirus (for example the SIV, HIV2 or FIV nuclear export system);
- a sequence favouring the nuclear import of RNA, for example the flap sequence [cPPT-CTS region (central polypurine tract-central termination sequence); cf. Charneau et al., Journal of Virology, May 1992; WO 01/27304] which enables effective nuclear import of the reverse-transcript vector genome; and
- a LTR 5' and 3', possibly modified, intervening in the transcription of packaged vector RNA.

The recombinant genome is preferably deleted from all of the lentiviral encoding sequences, in particular the viral genes encoding for the gag, pol and env sequences and the vif, vpr, vpu and nef accessory genes. The transcomplementing plasmid preferably keeps the tat and rev genes. The vector plasmid can advantageously include a LTR3' deleted from the U3 enhancer sequence (WO99/31251) so as to improve the expression of the transgene and the safety of the vector.

Another target can possibly be mutated in addition to the integrase mutations: the att sequences which are located at the ends of the DNA linear genome. If these sequences are mutated, the action of the integrase on the genome no longer happens correctly, and there can no longer be integration. The genome, which presents itself in the form of a linear DNA, can circularise.

The vectors and plasmids of the invention can be prepared from lentiviruses belonging to different species, in particular HIV-1, HIV-2, SIV, FIV, BIV, VISNA, CAEV, and EIAV. Particularly preferred serotypes are HIV, in particular HIV-1, FIV, EIAV and SIV.

The sequence of the transgene can be placed under the control of a chosen promoter and/or enhancer as well as of all the transcriptional, post-transcriptional and post-translational regulation elements necessary for good expression of said transgene.

In the sense of the invention, the term "transgene" generally indicates any encoding or non-encoding nucleic acid. This can be a non-encoding sequence such as, for example, an enzyme recognition sequence (specific integration site, site showing a particular affinity for a protein, etc.). This is preferably a sequence encoding a given polypeptide or a RNA which is active as such. It can in particular be a DNAc, a DNAg, a synthetic DNA, a RNA, for example an interferent RNA, a ribozyme etc., or a combination of the latter. Typically, the transgene is a DNA including a sequence encoding the desired expression product. Furthermore, the transgene can include one or more transcription termination regions, typically a polyadenylation signal.

The transgene can be chosen from a catalytic nucleic acid (interferent, antisense, ribozyme), a suicide nucleic acid (e.g. encoding a toxin) or a nucleic acid encoding a biologically active peptide, for example a growth factor, a trophic factor, an anti-angiogenic factor, an hormone, a cytokine, an antibody, a receptor, a differentiation factor, a colony stimulating factor, an anti-cancerous agent, an enzyme, a neurotransmitter or its precursor, etc.

According to one particular embodiment of the invention, the transgene encodes for example the following trophic factors: CNTF, NGF, NT3, NT4, FGF, PDGF, GDNF, etc., or anti-angiogenic factors or enzymes restoring a deficient metabolic activity or offering a particular metabolic function, for example: TH, AADC, GTPC, β-glucuronidase, etc.

According to another particular embodiment of the invention, the transgene encodes, for example, interferent RNAs (RNAi) which make it possible to specifically inhibit the expression of mutated proteins involved in a dominant genetic disease or in a disease induced by a function gain, for example a neurodegenerative disease such as mutated SOD (Amyotrophic Lateral Sclerosis), APP, tau, presenilin or BACE (Alzheimer's disease) proteins, α-synuclein (Parkinson's disease) or Huntingtin (Huntington's disease).

The transgene is typically placed under the control of a transcriptional promoter which can be homologous with respect to the transgene or heterologous, for example a cell, viral, synthetic, chimeric promoter, etc. The promoter used can be constitutive or regulated, weak or strong, tissue-specific or ubiquitary, dependent upon the 2 or 3 RNA polymerase, etc. One typically uses a viral promoter such as CMV, RSV LTR, TK, etc. or preferably a cell promoter such as PGK, Rho, EF1α etc. Specific tissue promoters can be used. These can be, for example ENO, GFAP, NSE promoters, a RNA polymerase III promoter such as the U6 or H1 promoter, possibly modified, etc. The promoter used to direct the transgene expression can be, for example, a viral promoter chosen from the promoter of the CMV, TK or RSV LTR gene.

The promoter present in the envelope plasmid and/or the promoter present in the vector plasmid are identical or different and cellular or viral.

Production of Non-Integrative and Non-Replicative Lentiviral Vectors

The lentiviral vectors according to the invention can be prepared in different ways, by transient transfection(s), in stable lines and/or by means of helper viruses.

The method according to the invention proposes, according to a particularly preferred embodiment, the combination of a minimum of three plasmids (cf. FIG. 1) in order to produce a recombinant virion or a recombinant lentivirus:

a) a transcomplementation plasmid, lacking any psi encapsidation signal and comprising a lentiviral gag sequence and a mutated lentiviral pol sequence encoding an integrase which is non-functional for the integration, said plasmid possibly being deleted from the vif, nef, vpu and/or vpr accessory genes, b) an envelope plasmid including a promoter-env-PolyA sequence, and c) a lentiviral vector plasmid including a recombinant genome, possibly deleted from the promoter region of LTR3' or of the LTR3' U3 enhancer sequence of, including, between the lentiviral LTR 5' and 3' sequences, a lentiviral encapsidation psi sequence, a RNA nuclear export element (preferably the HIV RRE or an equivalent element from any other retrovirus), a transgene and possibly a promoter and/or a sequence favouring nuclear import (cPPT CTS sequence for example) of RNA, as well as a mutated integrase preventing the integration of said genome into the genome of a host cell, said vector lacking any encoding sequence of the lentivirus, and the recovery of the lentivirus products.

Advantageously, the three plasmids used do not include any homologous sequence sufficient to enable recombination. The gag, pol and env encoding nucleic acids can advantageously be DNAc prepared according to the conventional techniques from sequences of viral genes available in the prior art and on data bases, and illustrated in the examples.

The transcomplementation plasmid provides a nucleic acid encoding the gag and pol lentiviral proteins. These proteins are derived from a lentivirus and, preferably, originate from VIH-1. The plasmid is lacking any encapsidation sequence, encoding sequence for an envelope, accessory genes, and advantageously is also lacking lentiviral LTRs. For this reason, the sequences encoding gag and pol proteins are advantageously placed under the control of a heterologous promoter, for example cellular, viral, etc., which can be constitutive or regulated, weak or strong. This is preferably a transcomplementing plasmid including a CMV-Δpsi-gag-pol-PolyA sequence. This plasmid enables expression of all the proteins necessary for the formation of empty virions, apart from the envelope glycoproteins. The transcomplementation plasmid can advantageously comprise the TAT and REV genes. Furthermore, the transcomplementation plasmid can also include a transcription regulation element chosen from WPRE, APP 5'UTR, TAU 3'UTR and a chromatin insulation sequence such as MAR (Matrix Attachment Region), SAR (Scaffold Attachment Region), scs and scs' (Special Chromatin Structure), etc. Advantageously, it is lacking in vif, vpr, vpu and/or nef accessory genes. Of course, the gag and pol genes as well as the TAT and REV genes can also be carried by the different, plasmids, possibly separated. In this case, several transcomplementation plasmids are used, each one encoding for one or more of said proteins.

The mutation in the pol sequence of the transcomplementation plasmid consists of one or more microdeletions of several bases, preferably in one or more point mutations affecting a basic region, the C-terminal region (for example a basic region of the C-terminal region), and/or the catalytic region of the encoded integrase sequence, as defined above.

The envelope plasmid provides a nucleic acid which enables the production of the chosen envelope (env) glycoprotein. It is lacking any psi encapsidation signal, gag or pol encoding sequences, and is also lacking lentiviral LTRs. It includes a promoter-env-PolyA sequence.

Pseudotyped VIH-1 vectors (including an envelope different from the wild-type envelope, originating for example from another virus, or of cellular origin, and thus possessing a modified tropism) described in the prior art include the envelope glycoprotein of the Vesicular Stomatitis Virus (VSV). This envelope has advantageous characteristics such as resistance to ultracentrifugation and a very wide tropism. Unlike other envelopes such as those of the classic retroviruses (the amphotropic and ecotropic MLV retroviruses or VIH gp120, but many others as well), the VSV glycoprotein is not labile after ultracentrifugation. This makes it possible to concentrate the viral supernatants and to obtain high infectious levels. Moreover, this envelope gives the virions a very wide tropism, in particular in vitro, enabling the infection of very many cell types. The receptor of this envelope would be a phosphatidylserine motif, present on the surface of numerous cells of different types.

The envelope (env) glycoprotein of the vesicular stomatitis virus (VSV-G) is advantageously used within the context of the invention, but any other pseudotype can be used in order to best target certain cell populations. The envelope protein can thus be chosen from any envelope glycoprotein from any enveloped virus, for example from a rhabdovirus envelope protein, more preferably lyssavirus, and even more preferably a serogroup virus of the rabies virus: Rabies (RAB), Duvenhague (DUV), European bat type 1 (EB-1), European bat type 2 (EB-2), Kotonkan (KOT), Lagos bat (LB), Obodhiang (OBD), Rochambeau (RBU), an envelope protein of a virus from the serogroup of the Mokola virus (MOK) and any chimeric composition of these envelopes. The rabies and Mokola viruses are particularly preferred. In fact they have a tropism in animal which is very specific to the nervous system (cf. WO 02/097104). Furthermore, this type of envelope enables the targeting of cells, in particular targeting of glial cells of the astrocytary type.

In a preferred embodiment, the invention uses lentiviral vectors, for example of the VIH-1 type, pseudotyped with a rabies or Mokola virus envelope.

A vector plasmid of the invention comprises a recombinant nucleic acid comprising between the LTR 5' and 3' the psi elements, RRE (or an equivalent element of another retrovirus), the transgene and possibly a promoter and/or the flap sequence, cPPT CTS. It can include, for example, the sequence 5'LTR-psi-RRE-cPPT CTS-(promoter-)transgene-LTR3'. The sequence of the transgene is possibly placed, within the vector plasmid, under the control of the promoter and/or of an enhancer, as well as of all the transcriptional, post transcriptional and post traductional regulation elements necessary for good expression of this gene. This plasmid includes the cis-acting viral sequences necessary for a good transduction process. From the original virus it only keeps certain sequences necessary for encapsidation of the genome (psi sequence of lentiviral origin), possibly the flap sequence (cPPT-CTS region) which enables efficient nuclear import of the reverse-transcript vector genome and an integral LTR 5' which enables transcription of the vector RNA before being packaged. Furthermore, this vector can possibly be deleted from the LTR 3' U3 enhancer sequence (WO 99/31251). Moreover, it is deleted from all of the original viral genes, in particular from the viral genes encoding the gag, pol and env sequences and from the accessory genes (vif, nef, vpr and/or vpu) in order to improve the safety of the vector.

In one particular embodiment of the invention, the att sequences which are located at the ends of the linear genome are furthermore advantageously mutated, and possibly deleted so as to make it more difficult for the integrase to act on the genome.

The promoters used in the transcomplementation plasmid, the envelope plasmid and in the vector plasmid in order to respectively promote the gag and pol expression of the envelope protein, of the vector genome mRNA and of the transgene are identical or different promoters advantageously chosen from ubiquitous or specific promoters, for example from the CMV, TK, RSV LTR viral promoters and a RNA polymerase III promoter, such as the U6 or H1 promoter.

The lentiviruses according to the invention are genetically modified such that certain genes constitutive of the native infectious virus are suppressed and replaced by a beneficial nucleic acid sequence to be introduced into the target cells. Following fusion of the virus to the cell membrane, said virus injects its nucleic acid into the cell. The genetic material transferred in this way in then transcribed and possibly translated into proteins within the host cell.

A preferred vector system according to the invention comprises:
  a) a transcomplementation plasmid, lacking any psi encapsidation signal and comprising a lentiviral gag sequence and a mutated lentiviral pol sequence encoding an integrase comprising a substitution of the $_{262}$RRK motif by AAH (in a basic region of the C-terminal region in the encoded sequence of the integrase), non-functional for the integration, said plasmid lacking any accessory genes such as vif, nef, vpu and/or vpr,
  b) an envelope plasmid as defined above, preferably including a viral promoter and encoding a VsV-G envelope, more preferably a CMV-VSV-G-PolyA sequence, and
  c) a lentiviral vector plasmid, possibly deleted from the promoter region of LTR3' or from the LTR3' U3 enhancer sequence including, between LTR 5' and 3', the psi elements, RRE, the transgene and possibly a promoter and/or the flap sequence, cPPT CTS, said vector lacking all of the lentivirus genes (for example HIV-1).

For the production of the non-integrative and defective recombinant viruses for replication, the plasmids described above can be introduced into competent cells, and the viruses produced are harvested. The cells used can be any competent cell, in particular eukaryotic cells, in particular from mammals, for example animals or humans. They can be somatic or embryonic, stem or differentiated. One can cite, for example, 293 cells, fibroblast cells, hepatocytes, muscular (skeletal, cardiac, smooth, blood vessel, etc.) cells, nerve cells (neurons, glials, astrocytes), epithelial, renal, ocular cells, etc. They can also be vegetable cells, yeasts or prokaryotic cells. They can also be cells transformed by means of the SV40 T antigene.

The invention is therefore based upon a method for preparing a non-integrative and non-replicative recombinant lentivirus, comprising the transfection of a population of competent cells with a combination of plasmids as described above, and recovery of the vectors produced.

The invention therefore relates to a particularly advantageous method for producing non-integrative and non-replicative lentiviruses enabling the in vivo expression of a transgene, comprising the transfection of competent cells by means of a non-integrative and non-replicative lentiviral vector system, as described above, comprising:
  a) at least one transcomplementation plasmid, lacking any psi encapsidation signal, and comprising a gag sequence and/or a pol sequence including a class 1 mutation, enabling,
for example, substitution of the $_{262}$RRK motif by AAH in a basic region and/or in the
C-terminal region of the encoded integrase sequence, said plasmid lacking any accessory
genes such as vif, nef, vpu and/or vpr.
b) an envelope plasmid including a (for example VSV-G)-PolyA (for example CMV-) envelope promoter sequence,
c) a vector plasmid, possibly deleted from the LTR3' U3 enhancer sequence, including between the 5' and 3' LTRs, the psi elements, RRE, the transgene and possibly a promoter and/or the flap sequence, cPPT CTS, said vector being deleted from the encoding sequences of the lentivirus (for example HIV-1), and
recovery of the lentivirus products.

The lentiviruses of the invention can also be prepared from lines of encapsidation cells producing one or more gag, env and/or pol proteins mutated on the integrase, as indicated above.

For this reason, in one particular embodiment, the method of the invention comprises the transfection of just two plasmids (the vector plasmid and the transcomplementation plasmid) in a line of cells expressing the chosen env protein. The cells used for preparing this line are, for example, the competent cells mentioned above.

According to another embodiment, the line used also expresses the env protein, the gag protein and/or the lentiviral pol protein, the latter comprising a class 1 mutation. In this case, the method comprises simply the transfection of the vector plasmid.

As indicated above, the lentiviruses produced preferably derive from the VIH-1, VIH-2, SIV, FIV, BIV, VISNA, CAEV or EIAV virus.

Of the cell lines one can in particular distinguish the DT40 line established from a hen lymphoma known for being very recombinable and the Cos 7 line (cells from a monkey kidney immortalised by means of an SV40 antigene). They can also be HCT116, DLD1 (human lines established from cells taken from a colorectal carcinoma), LF1 (human embryonic lung fibroblasts), LL1 (human embryonic skin fibroblasts), TK6 (human lymphoblastic line), HaCaT (human keratinocytes), U937 (human monocytes), HCT15, SW480, Colo320, Col15, EB, Hb1100, Rat-1, PC12 (rat photochromocytoma) etc. lines. This non-exhaustive list is given as an example. Other lines known to man of the art can be chosen and used within the context of the invention without any particular effort on his part.

In order to implement the methods of the invention, the plasmids can be introduced into the cells by any technique known to man of the art, adapted to the cell type in question. In general, the cells and the vector system are placed in contact in an appropriate device (plate, box, tube, pocket, etc.) for a sufficient period of time that enables transfer of the vector system or of the plasmid into the cells. Typically, the vector system or the plasmid is introduced into the cells by calcium phosphate precipitation, by electroporation, or by using one or more compounds that facilitate transfection, such as lipids, polymers, liposomes and peptides, etc. Calcium phosphate precipitation is preferred. The cells are cultivated in any adapted medium, such as RPMI, DMEM, a specific medium enabling a culture in the absence of foetal calf serum, etc.

One particular object of the invention also relates to a line of cells expressing, in a stable manner, a lentiviral integrase comprising one or more point mutations affecting a basic region, its C-terminal region (for example a basic region of the C-terminal region) and/or its catalytic site, said integrase being lacking integrative function, and to the use of this type of cell line for the in vitro preparation of non-integrative and non-replicative recombinant lentiviruses.

One object of the invention therefore relates to the cells obtained by implementing the method and the use of a cell, line or cell population according to the invention for preparing a cell composition used for implementing a therapeutic, vaccinal or surgical treatment method in humans or animals.

It also relates to kits for implementing methods for modifying the genome of cells in vitro or ex vivo, comprising a vector such as described above.

Applications

The viruses and lines according to the invention can be used, for example, for the expression of a transgene or of other nucleic acids, preferably in cells which do not divide or for the transient expression of a gene in division cells which are resistant to other transfection or even to transduction methods by other vectors.

Surprisingly, the present application shows that the lentiviral vectors obtained in this way are capable of transducing different cell types such as, for example, retinal cells, astrocytes, other glial cells or neurons. Other sub-populations of nerve cells which can be targeted by vectors of the invention are, for example, microglial cells, endothelial cells or oligodendrocytes. In one particular application relating to the transfer of genes in the eye, the vectors of the invention can be, for example, pseudotyped with the Mokola envelope so as to enable selective transfer to the pigment epithelial cells.

This non-integrative and non-replicative lentiviral vector is for improving the safety and efficiency of gene transfer: by mutating the integrase, the vector no longer integrates into the genome of the target cell, thus eliminating the risk of insertional mutagenesis. Moreover, possible insertion of the flap sequence (cPPT-CTS) into the vector can substantially improve the nuclear import of the DNA genome, enabling strong expression of the transgene, stable in the post-mitotic cells, and transient in the multiplying cells.

The possible applications of the non-integrative lentiviral vectors of the invention are of several types and include:
gene therapy, i.e. gene transfer in any mammal cell, in particular in human cells. These can be division cells or quiescent cells, cells belonging to central organs or to peripheral organs, such as the liver, the pancreas, a muscle, the heart etc. It is preferably a transfer of genes in quiescent cells (which do not divide), in particular in cells of the central nervous system, in particular of the brain, of the marrow and of the ocular sphere, for example within the context of treatment of neurodegenerative pathologies or of diseases of the retina, and a transfer of genes in division cells for transient expression (e.g.: anti-tumoral suicide strategy, axonal rejection strategy for treating traumas of the spinal cord).

Gene therapy can enable the expression of proteins, for example of neurotrophic factors, enzymes, transcription factors, receptors, etc. Moreover, it enables implementation of an "oligonucleotide" strategy (antisense or interferent RNAs, ribozymes, etc.),
cell therapy, i.e. the expression of differentiation factors in progenitor cells for orientating the cell towards a chosen destination prior to grafting or the ex vivo transduction of cells so that they express a beneficial factor, followed by the grafting of said cells.

One particular object of the invention relates to the use of a non-integrative and non-replicative lentivirus according to the invention for preparing a composition for the transfer of genes, for example into the central nervous system (including the ocular sphere) of a subject in vitro, ex vivo or in vivo, Another particular object of the invention relates to the use of this type of lentivirus for preparing a composition for the treatment of a disease affecting a central or peripheral organ, for example of a disease of the nervous system (including the ocular sphere).

According to the transgene that they contain, the non-integrative and non-replicative lentiviruses according to the invention can be used for producing a pharmaceutical composition for treating, for example, a neurodegenerative disease, and in particular Alzheimer's disease, Parkinson's disease, Huntington's disease, SLA or SMA, age-related macular degeneration (DMLA), ocular degeneration or traumas of the central nervous system (apoplexy, epilepsy, lesions or trauma of the spinal cord, etc.), diseases affecting the central nervous system (mucopolysaccharidoses, etc.), glioblastomas or astrocytomas, metabolic diseases affecting the nervous system (mucopolysaccharidoses, Charcot-Marie, etc.) or diseases affecting the ocular sphere (DMLA, pigment retinitis, glaucoma, etc.).

According to one particular embodiment of the invention, non-integrative and non-replicative recombinant lentiviruses are used for producing a pharmaceutical composition for treating pigment retinitis. The term "pigment retinitis" is a term used to indicate a heterogeneous group of ocular disorders characterised by progressive degeneration of the rods and cones (nerve cells of the retina) by apoptosis. With an incidence rate of 1 individual out of every 3,000, this is the main cause of blindness. The transduction of the cells of the pigment epithelium and of the photoreceptors is of crucial benefit in this type of pathology. A gene replacement strategy necessitates transduction of the photoreceptors or of the pigment epithelium, whereas a neuroprotection strategy could benefit from transduction of the pigment epithelium. In fact, the benefit of this method is that it does not modify the nerve cells, but only the pigment epithelium which will then synthesise a diffusible trophic factor, such as GDNF, and will secrete it in the area surrounding the photoreceptors to be protected.

Another object of the invention is the combined use of several lentiviruses for the purpose of transferring and expressing several nucleic acids in the cells of the nervous system. The combined use can comprise sequential administrations of the different viruses, or simultaneous administration.

As indicated above, the invention can enable the conveyance and expression of multiple nucleic acids in nerve cells, such as for example catalytic nucleic acids (interferent, antisense, ribozymes, etc.), nucleic acids encoding growth factors, trophic factors, cytokines, colony stimulation factors, anti-cancerous agents, toxins, enzymes, neurotransmitters or their precursors, etc.

The pharmaceutical composition containing the lentivirus according to the invention can be administered to a patient intracerebrally or systemically depending upon the particular tropism of the pseudotyped lentiviral vectors by means of an appropriate envelope glycoprotein. This can therefore be intracerebral, for example intra-striatal administration, into the hippocampus or the black substance, by intravenous, intra-arterial, intra-vitreal administration, or administered into the subretinal space, etc. Preferred injection methods are intra-cerebral injection and injection into the subretinal space.

The composition is advantageously administered at a level of between $10^2$ and $10^{10}$, typically between $10^3$ and $10^8$, effective particles for the transduction (level determined by cell transduction by series dilutions of the vector stock), or, with a genome equivalent, of between approximately $10^5$ and $10^{13}$ copies [level determined by quantitative reverse transcription PCR (polymerase chain reaction) on the RNA genome of the vector or by quantitative PCR on the DNA strand associated with the RNA genome of the vector]. The lentiviruses can be conditioned in any adapted solution, such as a saline, isotonic, buffered solution, possibly associated with stabilising agents such as isogenic albumin or any other stabilising protein, glycerol, etc., as well as adjuvant factors such as polybrene or DEAE dextran etc.

Other advantages of the invention are illustrated in greater detail in the following examples which must be considered as illustrative and non-restrictive.

EXPERIMENTAL PART

At first, the integrase sequences (fusioned with hemagglutinin), mutated or non-mutated in the transcomplementation plasmid used for producing lentiviral vectors (p8.91 INWT and p 8.91 INN plasmid) were used. Stocks of vectors derived from VIH-1 expressing green fluorescent protein (GFP) under the control of the precocious viral promoter of human cytomegalovirus (hCMV) and carrying the normal (INWT CMV GFP vector) or mutated (INN CMV GFP) integrase were then produced. A study relating to the efficiency of the INN CMV GFP vectors for managing the expression of the GFP transgene within nerve cells was finally carried out, first of all in vitro, and then in vivo.

Characterisation of the In Vitro Vector

Expression of the In Vitro GFP Transgene

In order to evaluate the capacity of a non-integrative lentiviral vector to transduce cell lines and to express a transgene here, 293T, HeLa and MT4 cells were incubated in the presence of different volumes of INWT CMV GFP and INN CMV GFP vectors. Seventy-two hours after transduction by the INWT CMV GFP integrative vector, a certain percentage of cells express GFP (analysis by FACS). In the same way, GFP+ cells were demonstrated by FACS 72 hours after transduction by the INN CMV GFP vector (FIG. 2). This first result suggests good transduction efficiency of the vectors of which the integrase has been inactivated.

Analysis of Pseudotransduction

During their production, the stocks of lentiviral vectors are contaminated by plasmidic DNA, in particular by the pTrip CMV GFP vector plasmid and by the GFP protein produced from this same plasmid in the transfected cells. These two elements can generate falsely positive cells in which the GFP does not come from the expression of the retrotranscribed vector genome. Therefore, these GFP+ cells are not transduced, but "pseudotransduced".

In order to demonstrate that the GFP+ cells do not result from a pseudotransduction mechanism, 293T cells were transduced, in the presence of or in the absence of any azidodeoxythymidine (AZT), with the help of a reverse-transcriptase (RT) inhibitor. In fact, treatment with AZT only inhibits the expression of GFP if the latter results from the transduction of cells. The percentage of GFP+ cells observed in the presence of AZT therefore corresponds to the percentage of pseudotransduction. After transducing 293T cells at an infection multiplicity (MOI) of 20, one observes 40.7% (±1.5) of GFP+ cells with the INWT CMV GFP integrative vector and 28.0% (±1.9) with the INN CMV GFP non-integrative vector. In the presence of 10 μM AZT, the percentage of transduced cells falls respectively to 5.8% (±0.1) and 4.9% (±0.4) (FIG. 3). Inhibition of the RT therefore makes it possible to reduce the percentage of GFP+ cells whether it be after transduction by the INWT CMV GFP integrative vector or by the INN CMV GFP vector. Most of the GFP+ cells observed in the absence of any reverse-transcriptase inhibitor are therefore effectively transduced by the two types of vectors and do not result from a pseudotransduction mechanism.

Stability of Expression in Division Cells

In order to verify the episomal character of the particles carrying the mutated IN-HAN integrase, the expression of GFP was analysed up to 15 days following transduction in the different HeLa, 293T and MT4 cell lines. The cells were transduced at a MOI of 5 by the mutant INN CMV GFP vector, by the integrative INWT CMV GFP control or by a non-integrative CMV GFP adenovirus control. Each batch of transduced cells was amplified for 12 to 15 days and analysed by FACS every 72 hours. Twenty-four hours before harvesting the last cells, some of these were treated with 5 mM sodium butyrate in order to evaluate the possible influence of hypoacetylation on the expression of GFP. The results obtained are shown in FIG. 4.

Over time, the percentage of 293T or MT4 cells expressing GFP is relatively stable when these are transduced with the INWT CMV GFP integrative control vector, this percentage falling slightly to the last points evaluated in the 293T cells (FIG. 4). However, treatment of the cells with sodium butyrate at the end of the experiment makes it possible to bring the percentage of 293T GFP+ cells back to the level initially measured, and this suggests reactivation of the promoter governing the expression of the transgene and shows the stability over time of the vector integrated into the population of cells analysed. In cells transduced with a non-integrative adenoviral control vector, the percentage of positive cells falls significantly during successive divisions such as to be cancelled out 15 days after transduction. In this case, the sodium butyrate treatment 15 days after transduction does not make it possible to re-establish the initial percentage of GFP+ cells (FIG. 4B). This result is explained by the progressive dilution of the adenoviral genomes during cellular divisions. As extrachromosomic elements, the vector genomes are not replicated like genomic DNA of the cell during the cell cycles. With each mitosis, a copy of the vector genome is therefore only transmitted to one of the two daughter cells, and this theoretically divides the percentage of cells expressing the transgene by 2 with each cell cycle.

Expression in the cells transduced by the vector carrying a mutant integrase shows a profile close to that observed after transduction with an adenoviral vector. In fact, the percentage of GFP+ cells reduces over time (FIG. 4) and can not be brought back to the initial level by treating the cells with sodium butyrate. This result suggests that, as in the case of transduction by an adenoviral vector, the genome of the INN CMV GFP vectors is eliminated from the cells initially transduced by successive dilution with each cell division.

Stability of the Expression of the GFP Transgene in Quiescent Cells

The reduction in the percentage of GFP+ cells over time could also reflect the instability of the vector genomes and their degradation in the nucleus of the transduced cells. In order to verify this hypothesis, the expression of the GFP transgene was studied after transduction of neuronal cells by the two types of vector. In fact, the primary neurons (embryonic rat cortex) do not divide in culture. Expression of GFP persists for at least 16 days after transduction of these cells with the INN CMV GFP vector (FIG. 5A and 5B). No significant difference could be observed between the percentage of immunoreactive cells transduced by the WT vector at the different times considered and that obtained with the N vector (2 factor ANOVA in repeated measures, p=0.9321). An additional experiment made it possible to show that expression of the transgene persists up to 25 days after transduction (FIG. 5C).

The episomal forms are therefore relatively stable in the nucleus of the transduced cells and enable expression of the transgene for at least 25 days in quiescent cells. This result supports the hypothesis of a reduction in the expression of GFP over time in division cells by dilution of the episomal vector genomes with each mitosis, rather than by degradation.

Expression of the GFP Transgene In Vivo

Expression in the Mouse Striatum

In order to determine the efficiency of the integrase-deficient lentiviral vectors in transducing cells in vivo and to enable expression of a GFP transgene, the INN CMV GFP vector was injected into the mouse striatum. Ten days after this injection, the GFP expression could be demonstrated. This expression lasts for a period of at least a month following injection. This result confirms the efficiency of the non-integrative vectors in enabling and maintaining the expression of a transgene in SNC cells (FIG. 6). In order to identify the phenotype of the transduced cells, co-marking by GFP/GFAP immunohistofluorescence (glial fibrillary acidic protein, astrocyte marker) on the one hand and GFP/NeuN (neuron marker) on the other hand was implemented on adjacent cuts. After analysis of the slides with a confocal microscope, majority colocalisation of GFP with the GFAP marker (FIG. 7A) and very little colocalisation of GFP with the NeuN marker (FIG. 7B) could be observed. These results suggest that in vivo the INN CMV GFP vector pseudotyped with the VSV envelope preferably transduces astrocytic cells.

Expression in the Retina

The capacity of the non-integrative lentiviral vector to transduce the pigment epithelial cells of the retina was evaluated. For this, subretinal injections of the vector were implemented in rats and in dogs. The preliminary results show expression of GFP for at least 9 weeks in rats and 3 months in dogs (FIG. 8). Evaluation of the stability of the expression in these two systems is being pursued. Results previously obtained by the inventors show that the lentiviral vectors essentially transduce, after subretinal injection in rats, the pigment epithelial cells.

A low level of toxicity was observed in some dogs by closely examining the eye. This toxicity is independent of the injected dose, and so of the vector itself, and seems induced by the surgical act at the time of the injection. A more extensive histological analysis will make it possible to understand this irritation more clearly.

Expression of a Therapeutic Transgene in an Animal Model

With the aim of validating the use of a non-integrative lentiviral vector for a clinical application, the efficiency of said vector in expressing a therapeutic transgene, the Glial-derived neurotrophic factor (GDNF) was tested after subretinal injection in RD10 rats, a model characterised by pigment retinitis. The expression "pigment retinitis (RP)" indicates a heterogeneous group of ocular disorders characterised by progressive degeneration, by apoptosis of the rods and cones (nerve cells of the retina). With an incidence rate of one individual out of every 3000, this is the main cause of blindness. Transduction of the pigment epithelial cells and of the photoreceptors is of crucial interest in this type of pathology. A gene replacement strategy necessitates transduction of the photoreceptors or of the pigment epithelium, whereas a strategy of neuroprotection could benefit from transduction of the pigment epithelium. In fact, this method has the benefit that it does not modify the nerve cells, but only the pigment epithelium which will then synthesise a diffusible neurotrophic factor, such as GDNF, and will secrete it in the area surrounding the photoreceptors to be protected.

The experiments carried out in the laboratory show that integrative lentiviral vectors are efficient for transducing cells of the pigment epithelium by means of subretinal injection in normal mice.

The results indicated above show the efficiency and the therapeutic potential of the non-integrative lentiviral vectors according to the invention capable of enabling expression of a transgene in vitro, ex vivo and in vivo in the central nervous system (brain and retina), in rodents and in large animals.

The invention claimed is:

1. A non-replicative and non-integrative recombinant lentivirus comprising (i) a recombinant lentiviral genome which does not encode any lentiviral proteins, comprising a 5' and a 3' LTR sequence flanking: a lentiviral encapsidation psi sequence, a RNA nuclear export element, a transgene, as well as (ii) a mutated HIV-1 lentiviral integrase wherein the mutation abolishes integrative function of the integrase thereby preventing the integration of the recombinant genome into the genome of a host cell, the mutation consisting of one or more point mutations in the L, Q and/or N regions of the C-terminal basic region of the HIV-1 integrase.

2. The lentivirus according to claim 1, wherein the recombinant genome further comprises a sequence enabling effective nuclear import of RNA.

3. The lentivirus according to claim 2, wherein the sequence enabling effective nuclear import of RNA is cPPT CTS.

4. The lentivirus according to claim 1, wherein said lentivirus is obtained from HIV-1, HIV-2, SIV, FIV, EIAV, BIV, VISNA and CAEV.

5. The lentivirus according to claim 4, wherein the lentivirus is obtained from HIV-1 and the one or more point mutations is a substitution of the $_{262}$RRK motif by an AAH motif in the HIV-1 integrase sequence.

6. The lentivirus according to claim 1, wherein the RNA nuclear export element comprises the REV responsive element (RRE sequence) of HIV-1.

7. The lentivirus according to claim 1, wherein the transgene is a catalytic nucleic acid (interferent, antisense, ribozyme), a suicide nucleic acid or a nucleic acid encoding a biologically active polypeptide.

8. The lentivirus according to claim 1, wherein the transgene is a nucleic acid encoding a growth factor, a trophic factor, a hormone, a cytokine, an antibody, a receptor, a differentiation factor, a colony stimulation factor, an anticancerous agent, a toxin, an enzyme, a neurotransmitter or its precursor.

9. The lentivirus according to claim 1, wherein the lentivirus is obtained from HIV-1 and the one or more point mutations is a substitution of amino acid 186 in the L region of the C-terminal basic region.

10. The lentivirus according to claim 1, wherein the lentivirus is obtained from HIV-1 and the one or more point mutations are Q214L substitution and/or a Q216L substitution in the Q region of the C-terminal basic region.

11. A pharmaceutical composition comprising (a) a non-replicative and non-integrative recombinant lentivirus comprising (i) a recombinant lentiviral genome which does not encode any lentiviral proteins, comprising a 5' and a 3' LTR sequence flanking: a lentiviral encapsidation psi sequence, a RNA nuclear export element, a transgene, as well as (ii) a mutated HIV-1 lentiviral integrase wherein the mutation abolishes integrative function of the integrase thereby preventing the integration of the recombinant genome into the genome of a host cell, the mutation consisting of one or more point mutations in the L, Q and/or N basic regions of the C-terminal basic region of the HIV-1 integrase, and (b) a pharmaceutically acceptable excipient.

12. The pharmaceutical composition according to claim 11, wherein the recombinant genome of the lentivirus further comprises a sequence enabling effective nuclear import of RNA.

* * * * *